United States Patent

Maiorana et al.

[11] Patent Number: 4,547,495
[45] Date of Patent: Oct. 15, 1985

[54] 1,5-BENZOTHIAZEPINES WITH CARDIOVASCULAR UTILITY, AND PHARMACEUTICAL COMPOSITIONS CONTAINING THEM

[75] Inventors: Stefano Maiorana, Milan; Diego G. Brocchetti, Brescia; Giuseppe Piacenza, Turin, all of Italy

[73] Assignee: Schiapparelli Farmaceutici S.p.A., Turin, Italy

[21] Appl. No.: 628,730

[22] Filed: Jul. 9, 1984

[30] Foreign Application Priority Data

Jul. 22, 1983 [IT] Italy .................. 22185 A/83

[51] Int. Cl.$^4$ .................. C07D 417/12; A61K 31/55
[52] U.S. Cl. .................. 514/211; 260/239.3 B
[58] Field of Search .................. 260/239.3 B; 424/275

[56] References Cited

PUBLICATIONS

Kugita et al., "Chem. Pharm. Bull.", vol. 19, (1971) pp. 595-602.

Primary Examiner—Robert T. Bond
Attorney, Agent, or Firm—Buchnam and Archer

[57] ABSTRACT

New 1,5-benzothiazepines of the following general formula

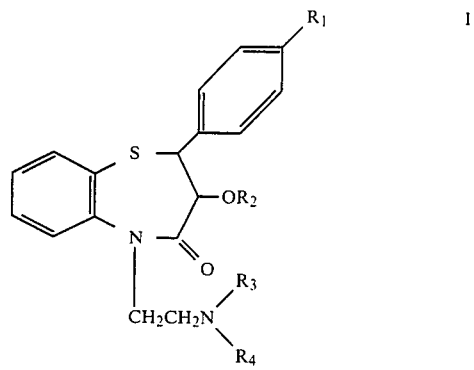

wherein:
$R_1$ represents $(C_{1-4})$alkyl, $(C_{1-4})$alkoxy or a halogen atom;
$R_2$ is selected from: benzoyl independently substituted with 1 to 3 $(C_{1-4})$alkyl or $(C_{1-4})$alkoxy groups, or with halogen atoms; phenylcarbamoyl; phenylcarbamoyl independently substituted with 1 to 3 $(C_{1-4})$ alkyl or $(C_{1-4})$ alkoxy groups or with halogen atoms; the groups $R_5$-CO, in which $R_5$ is the radical deriving from a heterocyclic ring optionally substituted by a $(C_{1-4})$alkyl or a $(C_{1-4})$alkoxy radical, or by a halogen atom;
$R_3$ and $R_4$ independently represent $(C_{1-4})$alkyl groups; and salts therewith of pharmaceutically acceptable acids.

The compounds of the invention possess cardiovascular utility.

15 Claims, No Drawings

1,5-BENZOTHIAZEPINES WITH CARDIOVASCULAR UTILITY, AND PHARMACEUTICAL COMPOSITIONS CONTAINING THEM

BACKGROUND OF THE INVENTION

The 1,5-benzothiazepine ring represents a heterocyclic moiety well known from the art. 1,5-Benzothiazepine-4-one derivatives bearing a double bond between the 2 and 3 positions and substituted at the positon 3 by alkyl, alkoxy, halo or trifluoromethyl are described in U.S. Pat. Nos. 3,895,006 and 3,983,106. These compounds are said to possess an antidepressant activity. Other 1,5-benzothiazepine-4-one derivatives are known from U.S. Pat. No. 3,646,008, in which 3-alkoxycarbonyloxy-1,5-benzothiazepine-4-one compounds are claimed, and U.S. Pat. No. 3,562,257 in which the substituents at the position 3 of the 1,5-benzothiazepine nucleus is a lower aliphatic acyloxy group from 1 to 4 carbon atoms. 3-Acyloxy-1,5-benzothiazepine-4-ones, in which the 3-acyloxy group is other than lower aliphatic acyl, as well as 3-phenyl or 3-(substituted phenyl)-carbamoyloxy-1,5-benzothiazepine-4-ones are, however, completely new.

SUMMARY OF THE INVENTION

The present invention refers to new 1,5-benzothiazepines of the following formula,

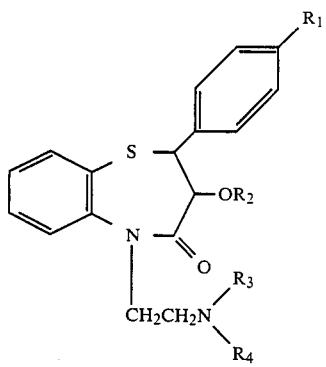

wherein:
$R_1$ represents $(C_{1-4})$alkyl, $(C_{1-4})$alkoxy or a halogen atom;
$R_2$ is selected from: benzoyl independently substituted with 1 to 3 $(C_{1-4})$alkyl or $(C_{1-4})$alkoxy groups, or with halogen atoms; phenylcarbamoyl; phenylcarbamoyl independently substituted with 1 to 3 $(C_{1-4})$alkyl or $(C_{1-4})$alkoxy groups or with halogen atoms; the group $R_5$—CO, in which $R_5$ is the radical deriving from a heterocyclic ring optionally substituted by a $(C_{1-4})$alkyl or a $(C_{1-4})$alkoxy radical, or by a halogen atom;
$R_3$ and $R_4$ independently represent $(C_{1-4})$alkyl groups. The compounds of the invention possess cardiovascular utility.

A second object of the present invention is represented by the pharmaceutically acceptable acid addition salts of the compounds of formula I such as, for instance, the hydrochloride, the hydrobromide, the hydroiodide, the sulphate, the phosphate, the perclorate, the nitrate, the acetate, the tartrate, the citrate, the succinate, the maleate, the methansulfonate, the benzenesulfonate, the 4-methylsulfonate, the napsylate and the analogs.

A further object of the present invention is the use of the compounds of formula I in the treatment of cardiovascular diseases.

Still a further object of the present invention is represented by pharmaceutical compositions useful for combatting cardiovascular diseases, containing, as the active ingredient, a suitable amount of a compound of formula I, or a salt therewith of a pharmaceutically acceptable acid, and one or more conventional excipients. As used herein, the term "$(C_{1-4})$alkyl" designates linear or branched alkyl groups like methyl, ethyl, propyl, isopropyl, butyl, isobutyl, sec.-butyl or tert.-butyl, whereas "$(C_{1-4})$alkoxy" essentially means methoxy, ethoxy, propoxy, isopropoxy, butoxy, sec.-butoxy, isobutoxy and tert.-butoxy. The terms "halogen atom" and "halogen atoms" refer essentially to chlorine, bromine, fluorine and iodine. With the expression "heterocyclic ring" it is intended to designate a heterocyclic ring selected from pyrrole, furan, thiophene, pyridine, indole, isoindole, benzofuran, quinoline and isoquinoline, as well as the corresponding, totally or partially hydrogenated counterparts. Thus, for instance, the group $R_5$—CO may be defined as pyrrolylcarbonyl, furylcarbonyl or furoyl, thienylcarbonyl or thenoyl, pyridylcarbonyl, indolylcarbonyl, isoindolylcarbonyl, quinolylcarbonyl and isoquinolylcarbonyl. When $R_5$ is 3-pyridyl, the group $R_5$—CO is also called nicotinoyl.

A preferred group of compounds comprises those compounds of formula I wherein $R_1$ is $(C_{1-4})$alkoxy, $R_2$ is the group $R_5$—CO in which $R_5$ represents pyrrolyl, furanyl, thienyl, pyridyl, quinolyl, pyrrolidinyl or piperidinyl, and $R_3$ and $R_4$ independently represent $(C_{1-4})$alkyl, and salts therewith of pharmaceutically accetable acids.

A second preferred group of compounds comprises those compounds of formula I wherein $R_1$ is $(C_{1-4})$alkoxy, $R_2$ is the radical $R_5$—CO in which $R_5$ is 3-pyridyl, $R_3$ and $R_4$ independently represent $(C_{1-4})$alkyl, and salts therewith of pharmaceutically acceptable acids.

A third preferred group of compounds comprises those compounds of formula I wherein $R_1$ represents $(C_{1-4})$alkoxy or a halogen atom, $R_2$ is benzoyl substituted with 1 to 3 $(C_{1-4})$alkoxy groups or halogen atoms, $R_3$ and $R_4$ independently represent $(C_{1-4})$alkyl, and salts therewith of pharmaceutically acceptable acids.

A further preferred group of compounds comprises those compounds of formula I wherein $R_1$ represents $(C_{1-4})$alkyl or $(C_{1-4})$alkoxy, $R_2$ stands for phenylcarbamoyl or phenylcarbamoyl substituted by 1 to 3 $(C_{1-4})$alkoxy groups or halogen atoms, $R_3$ and $R_4$ independently represent $(C_{1-4})$alkyl, and salts therewith of pharmaceutically acceptable acids.

The compounds of formula I above possess two asimmetry centers, namely those corresponding to the two carbon atoms bearing the

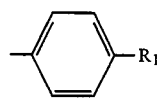

and the $OR_2$ substituents respectively. Accordingly, they may exist as enantiomeric and diastereo isomeric forms, and the present invention wants to refer both to the single separated isomers and to their mixtures in different mutual ratios. In addition, each of these enantiomeric and diastereoisometric forms may exist as one of the possible geometric configurations cis and trans, which are equally included within the scopes of the present invention.

The compounds of formula I are prepared by reacting a substance of formula

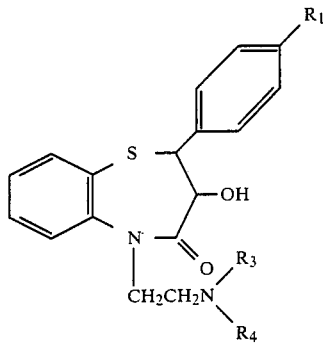

wherein $R_1, R_3$ and $R_4$ are as above defined, or one of the possible enantiomeric or diastereoisomeric forms, in one of the possible geometric configurations cis or trans, with a suitable agent capable of introducing substituent $R_2$.

Thus, for instance, a general method for preparing the compounds of the present invention comprises reacting a molar amount of the substance of formula II above, or a salt thereof, with from about 1 to about 4 and, preferably, from about 1 to about 3 molar proportions of an acylating or carbamoylating agent selected from a benzoyl halide, preferably a benzoyl chloride, a benzoic anhydride, a mixed benzoic anhydride, wherein the benzoyl and benzoic portions are independently substituted by 1 to 3 ($C_{1-4}$)alkyl or ($C_{1-4}$)alkoxy groups or by halogen atoms, phenylisocyanate, a phenylisocyonate independently substituted by 1 to 3 ($C_{1-4}$)alkyl or ($C_{1-4}$)alkoxy groups or by halogen atoms, $R_5$—CO hal wherein $R_5$ is as above defined and hal represents a halogen atom, preferably chlorine, and $R_5$—CO—X, wherein $R_5$ is again as above defined and X may be the group $R_5$—CO—O or the residue typical of a mixed anhydride.

The reaction is carried out in the presence of an inert organic solvent like benzene, toluene, tetrahydrofuran, dioxane and the analogs and, when a benzoyl halide or a compound of formula $R_5$—CO-hal is used as the acylating agent, also in the presence of an organic base like triethylamine, in order to block the acidity which forms during the reaction.

The reaction is carried out at a temperature varying from about room temperature and about 60° C. In general, a temperature interval comprised between about room temperature and about 50° C. is sufficient for achieving the best results. A time range from about 5 to about 30 hours is required to bring the reaction to completion.

The end products are recovered from the reaction medium by means of conventional procedures and, if desired, may be transformed into the corresponding acid addition salts by reaction with the predetermined pharmaceutically acceptable acid.

The preparation of the compounds of formula II was described in U.S. Pat. No. 3,562,257. The compounds of formula II as the isomers (+)-2,3cis, useful for preparing some of the optically active compounds of the invention, were prepared by subjecting the compound cis-(+)-3-acetoxy-5-[2-(dimethylamino)ethyl]-2,3-dihydro-2-(4-methoxyphenyl)-1,5-benzothiazepine-4(5H)-one, as the free base or as its hydrochloride, to mild alkaline hydrolysis under hydroalcoholic conditions.

This is a substance known from the literature, see for instance Arzn. Forsch., 21(9), 1338, 1971.

As stated above, the compounds of formula I possess cardiovascular utility. More specifically, they are endowed with a high degree of calcium antagonist activity and elicit a marked coronarodilating action. They are therefore useful in the treatment of heart diseases like myocardial ischemia and angina pectoris and, in general, of all those cardiac pathologic situations ascribable to coronary insufficiency. Surprisingly, these favorable coronarodilating properties are not coupled with any depressant action in the cardiac muscle, so that the compounds according to the invention can be employed without substantial risk of causing undesired and often fatal side-effects in the treated subjects.

These biological properties were investigated by means of in vitro and in vivo tests, the results of which are hereinbelow reported. In these experiments, the compound of Example 1 was selected as the representative member of the class of substances embraced by formula I above, whereas a structurally related compound, namely the cis-(+)-3-acetoxy-5-[2-(dimethylamino)ethyl]-2,3-dihydro-2-(4-methoxyphenyl)-1,5-benzothiazepine-4(5H)-one hydrochloride, a calcium antagonist and coronarodilator known from the literature (see above reference from Arzn. Forsch.) was taken as the comparison substance: it will hereinafter be referred to as Compound A.

The in vitro experiments were carried out on isolated guinea pig hearts, perfused with cumulative administrations of the compounds to be tested, substantially according to the well known Langendorff's technique (O. Langendorff, Pfluegers, Arch., 61,291,1895). The compounds were administered at dosages of 0.05–0.5 and 5μ isolated heart, suspended in 0.5 ml of the perfusion liquid, and the effects of each administration were followed for 20 minutes before giving the subsequent dose.

The effects on the following parameters were recorded, namely:
DP=Developed Pressure
CPP=Coronary Perfusion Pressure
HR=Heart Rate The obtained results are reported in the following table, and are expressed as % variations over the basal values i.e., the values recorded by the sole administration of the perfusion liquid. Each value is the mean of six determinations.

TABLE 1

| PARA-METER | COM-POUNDS | DOSAGES (mg/% isolated heart) | | |
| --- | --- | --- | --- | --- |
| | | 0.5% variations | 0.5% variations | 5% variations |
| DP | Example 1 | −15 | −19 | −25 |
| | Compound A | −28 | −30 | −40 |
| CPP | Example 1 | −7 | −10 | −14 |
| | Compound A | −5 | −6 | −6.5 |
| HR | Example 1 | −2.5 | −3.5 | −5 |
| | Compound A | −2 | −3.5 | −18 |

The above data are a first indication of the excellent coronarodilating properties of the compound of Example 1 which shows a significantly higher reduction of CPP with respect to Compound A. In addition, the lack of cardio-depressive action is already evident in these preliminary in vitro tests, being the reduction of the DP i.e., a parameter related to the contractile force of the cardiac muscle, and of the HR much less marked for the compound of the invention than for the reference substance. The reduction of the HR developped by the compound of Example 1 appears indeed to be negligible.

These in vitro results were confirmed by in vivo experiments carried out on the anesthetized open-chest dog.

In these experiments, two groups of 8 mongrel dogs each, weighing 14-25 Kg, were anesthetized with sodium thiopental and surgically opened according to the known laboratory techniques employed for recording the heemodynamic parameters of a compound to be tested.

The compound of Example 1 was dissolved in aqueous 0.01N hydrochloric acid containing 0.9% by weight of NaCl, and the pH was adjusted to about 6 by means of 1N NaOH. The ineffectiveness of the solvent was tested on every dog. Compound A was dissolved in saline. The substances were administered intravenously over 1 minute at dosages of 0.25-0.5 and 0.75 mg/kg. The effects of each administration were monitored for 20 minutes before a subsequent administration were given. A group of animals received the compound of Example 1, the other group was administered with the reference substance. The effects on the following group of parameters were recorded:

(1) Coronary Flow (CF) and Coronary Resistances (CR)
(2) Left Ventricular Pressure (LVP) and $dP/_{dt}$ max i.e., the variation of the pressure in the left ventricle as a function of the time
(3) Heart Rate (HR), PR and QRS, wherein P,Q,R and S are conventional letters assigned to the various peaks monitored in a standard electrocardiogram, see A. Katz, Physiology of the Hearth, R even Press, New York, 1977, page 264. PR represents the interval of time (in seconds) required by the electrical impulse which triggers the mechanical contractions, originating from the SA node (Synus Atrial node) to reach the right ventricle and is thus a measure of the atrio-ventricular (AV) conductivity, whereas QRS is related to the conductivity of the same impulse in the right ventricle.

Both the parameters under (2) and those under (3) are related to the myocardial functionality, whereas the parameters under (1) are a direct measure of the coronarodilating properties of the tested compounds.

The obtained results are reported in the following tables and are expressed as the % variations over the basal values i.e., the values recorded at the beginning of the experiment. As stated above, each value is the mean of eight determinations.

TABLE 2

| PARA-METER | COM-POUNDS | (Group 1) DOSAGES (mg/kg i.v.) | | |
|---|---|---|---|---|
| | | 0.25% variation | 0.50% variation | 0.75% variation |
| CF | Example 1 | +23 | +39 | +40 |
| | Compound A | +21 | +30 | +29 |
| CR | Example 1 | −27 | −36 | −32 |

TABLE 2-continued

| PARA-METER | COM-POUNDS | (Group 1) DOSAGES (mg/kg i.v.) | | |
|---|---|---|---|---|
| | | 0.25% variation | 0.50% variation | 0.75% variation |
| | Compound A | −29 | −44 | −48 |

TABLE 3

| PARA-METER | COM-POUNDS | (Group 2) DOSAGES (mg/Kg i.v.) | | |
|---|---|---|---|---|
| | | 0.25% variation | 0.50% variation | 0.75% variation |
| LVP | Example 1 | −4 | −4 | −2 |
| | Compound A | −10 | −13 | −16 |
| $dP/_{dt}$ max | Exaxple 1 | −2 | −6 | −9 |
| | Compound A | −14 | −18 | −28 |

TABLE 4

| PARA-METER | COM-POUNDS | (Group 3) DOSAGES (mg/Kg i.v.) | | |
|---|---|---|---|---|
| | | 0.25% variation | 0.50% variation | 0.75% variation |
| HR | Example 1 | +2 | −2 | −6 |
| | Compound A | −7.5 | −29 | −42 |
| PR | Example 1 | +1.5 | +2.6 | +5.1 |
| | Compound A | +22 | +67 | +84 |
| QRS | Example 1 | −0.8 | −3.9 | −2.5 |
| | Compound A | +8 | +16 | +14 |

As it can be seen from Table 2, the compound of Example 1 displays outstanding coronarodilating properties, both in term of increase of the coronary blood flow and decrease of the coronary resistances. Moreover, this beneficial effects on the coronary circulation are not coupled with any depressant activity on the cardiac muscle, being the parameters related to the contractility and beats frequency (TABLES 3 and 4) poorly influenced by the compound of the invention. This specificity of action toward the coronary circulation and resistances elicited by this substance is of considerable therapeutic value, as, for instance, in certain situations like myocardial ischemia, a further decrease of the ventricular function may even have a fatal outcome. In addition, the lack of influence on the PR and QRS conduction times (TABLE 4) is a clear evidence that, unlike the reference substance, the compound of Example 1 has practically no detrimental effect on the atrio-ventricular conduction when administered at the effective coronarodilating dosages. This implies that such compound can in principle be given safely to coronary patients suffering from disturbances in the atrio-ventricular conduction, whereas other substances not displaying such a specific action at coronary level have to be managed with extreme caution.

In general, it can be concluded that the invention substances represent potentially useful drugs in the treatment of angina pectoris and myocardial ischemia in those cases in which the cardiac contractility and electrophisiology are already depressed, like myocardial infarction, cardiac decompensation, synus bradycardia and atrio-ventricular block.

The use of the new compounds of the invention as cardiovascular agents and, in particular, as coronarodilating agents refers to all of the industrially applicable acts and aspects of said use, including their embodiment into pharmaceutical compositions. As stated above, the pharmaceutical compositions containing the active compounds are in fact a further specific object of the invention.

The compounds of the invention may therefore be administered by various routes, as an example the oral, inhalatory, intravenous or intramuscular one and, preferably, by oral route. To illustrate, for oral administration, the compounds are formulated as tablets, dispersible powders, capsules, sugar-coated tablets, granules, syrup, elixirs, solutions or aeresols. The compositions for oral use are prepared as known in the art and may contain one or more conventional adjuvants such as, for instance, sweetening agents, flavoring agents, coloring agents, coating and preservative agents, in order to provide an elegant and palatable preparation. Tablets may contain the active ingredient admixed with the conventional, pharmaceutically acceptable excipients, e.g. inert diluents, such as calcium carbonate, sodium carbonate, lactose and talc, granulating and disintegrating agents, such as, for instance, starch, alginic acid and sodium carboxymethylcellulose, binding agents, e.g., starch, gelating, gum arabic and polyvinylpyrrolidone and lubricating agents, e.g. magnesium stearate, stearic acid and talc.

Also syrups, elixirs and solutions are prepared as known in the art. Together with the active ingredient they may contain suspending agents such as, for instance, methylcellulose, hydroxyethylcellulose, tragacanth and sodium alginate, wetting agents, e.g. lecithin, polyoxyethylene stearates and polyoxyethylene sorbitan monooleate, and the common preservative, sweetening and buffering agents.

The dosage of active ingredient useful in the treatment of diseases due to coronary insufficiency may vary within wide limits, depending on the nature of the ingredient. In general, good coronarodilating effects are achieved by adminsitering the compounds of the invention at daily dosages varying from about 2 to about 5 mg/Kg of body weight.

The pharmaceutical dosage forms generally contain from about 50 to about 150 mg of active ingredient in admixture with one or more usual solid or liquid pharmaceutical carriers and are suitable for single or multiple daily administrations.

The following examples illustrate the invention and describe in detail some compounds of formula I without limiting the scope of the invention itself.

(A) Preparation of the starting compound cis-(+)-2,3-dihydro-5-[2-(dimethylamino)ethyl]-3-hydroxy-2-(4-methoxyphenyl)-1,5-benzothiazepine-4(5H)-one 30 Grams (0.0665 mole) of cis-(+)-3-acetoxy-2,3-dihydro-5-[2-(dimethylamino)ethyl]-2-(4-methoxyphenyl)-1,5-benzothiazepine-4(5H)-one hydrochloride were added to a solution of 7.5 g (0.1337 mole) of potassium hydroxide in 450 ml of ethanol. The resulting mixture was kept at room temperature for 90 minutes, then the solvent was evaporated off in vacuo, the residue was taken up with water and subsequently extracted with $CHCl_3$. The organic phase wase washed with water, in order to remove the excess of alkali, then dried over sodium sulfate. After evaporating the solvent under vacuum, 24.26 g of a glassy paste which became solid upon standing overnight at room temperature was obtained. It was finally ground and used as such for the subsequent reactions.

M.p.=86°–87° C. $[\alpha]_D^{20}=+142.2°$ (C=1% in $CH_3OH$)

EXAMPLE 1

Cis-(+)-2,3-dihydro-5-[2-(dimethylamino)ethyl]-2-(4-methoxyphenyl)-3-nicotinoyloxy-1,5-benzothiazepine-4(5H)-one 7 Grams (0.0188 mole) of the compound prepared under (A) were dissolved in 80 ml of anhydrous benzene, and the resulting solution was added with 8 ml (0.0574 mole) of triethylamine and 5 g (0.0281 mole) of nicotinoylchloride suspended in 20 ml of anhydrous benzene. The reaction mixture was heated for 24 hours on an oil bath at 55°–60° C. under stirring then, after cooling, it was twice washed with water and the organic phase was dried over sodium sulfate. The organic solvent was removed in vacuo until formation of a precipitate then, after complete precipitation, the obtained solid was recovered by filtration, washed with anhydrous diethyl ether and dried overnight at 70° C.

Yield: 7.18 g

M.p.=159.5°–161° C. $[\alpha]_D^{20}=+57°$ (C=1% in $CH_3OH$).

EXAMPLE 2

Cis-(+)-2,3-dihydro-5-[2-(dimethylamino)ethyl]-3-[(4-fluoro)-phenylcarbamoyloxy]-2-(4-methoxyphenyl)-1,5-benzothiazepine-4(5H)-one 10 Grams (0.268 mole) of the compound prepared under (A) were dissolved in 100 ml of anhydrous benzene and subsequently added with 3.02 ml (0.0269 mole) of 4-fluoro-phenylisocyanate, then the resulting solution was stirred on an oil bath at 30°–35° C. for 7 hours. After evaporating the solvent, the residue was taken up with anhydrous diethyl ether and the obtained white precipitate was recovered by filtration.

Yield: 9,5 g of the title compound.

M.p.=153°–54° C. $[\alpha]_D^{20}=+60.7°$ (C=1% in $CH_3OH$)

EXAMPLE 3

Cis-(+)-2,3-dihydro-5-[2-(dimethylamino)ethyl]-3-[(3-fluoro)-phenylcarbamoyloxy]-2-(4-methoxyphenyl)-1,5-benzothiazepine-4(5H)-one The title compound was prepared substantially as described in the foregoing examples, by using 3-fluoro-phenylisocyanate instead of the 4-fluoro isomer.

Yield: 10.5 g

M.p.=111°–13° C. $[\alpha]_D^{20}=+44.2°$ (C=1% in DMSO) DMSO=Dimethylsulfoxide

EXAMPLE 4

Cis-(+)-2,3-dihydro-5-[2-(dimethylamino)ethyl]-2-(4-methoxyphenyl)-3-(phenylcarbamoyloxy)-1,5-benzothiazepine-4(5H)-one The title compound was prepared substantially as described in Example 2, by using phenylisocyanate instead of 4-fluorophenylisocyanate and heating for 24 hours instead of 7 hours.

Yield=12 g

M.p.=106°–8° C. $[\alpha]_D^{20}=+50.3°$ (C=1% in DMSO) DMSO=Dimethylsulfoxide

EXAMPLE 5

Cis-(+)-2,3-dihydro-5-[2-(dimethylamino)ethyl]-2-(4-methoxyphenyl)-3-(3,4,5-trimethoxybenzoyloxy)-1,5-benzothiazepine-4(5H)-one 8 Grams of the compounds prepared under (A) were dissolved in 80 ml of benzene and the resulting solution was added with 3.3 ml (0.0237 mole) of triethylamine and 4.95 g (0.0215 mole) of 3,4,5-trimethoxybenzoyl chloride. The reaction solution was stirred at 35° C. on an oil bath for 28 hours then after cooling, was washed three times with water and subsequently dried over sodium sulfate. The solvent was evaporated off in vacuo, the obtained residue was taken up with anhydrous diethyl ether and the formed white precipitate was recovered by filtration.

Yield: 9,8 g

M.p.=139°–41° C. $[\alpha]_D^{20}$=44.3° (C=1% in DMSO) DMSO=Dimethylsulfoxide

Other representative compounds of the invention which can be obtained according to the foregoing procedures are hereinbelow reported.

Cis-(+)-2,3-dihydro-5-[2-(dimethylamino)ethyl]-2-(4-methoxyphenyl)-3-(2-thenoyloxy)-1,5-benzothiazepine-4(5H)-one Cis-(+)-2,3-dihydro-5-[2-(dimethylamino)ethyl]-3-(2-furoyloxy)-2-(4-methoxyphenyl)-1,5-benzothiazepine-4(5H)-one Cis-(+)-2-(4-butoxyphenyl)-2,3-dihydro-5-[2-(dimethylamino)ethyl]-3-nicotinoyloxy-1,5-benzothiazepine-4(5H)-one Cis-(+)-2,3-dihydro-5-[2-(dimethylamino)ethyl]-2-(4-methoxyphenyl)-3-(2-pyrrolidinylcarbonyloxy)-1,5-benzothiazepine-4(5H)-one Cis-(+)-2,3-dihydro-5-[2-(dimethylamino)ethyl]-2-(4-methoxyphenyl)-3-(2-pyrrolylcarbonyloxy)-1,5-benzothiazepine-4(5H)-one Cis-(+)-2,3-dihydro-5-[2-(diethylamino)ethyl]-2-(4-methoxyphenyl)-3-nicotinoyloxy-1,5-benzothiazepine-4(5H)-one Cis-(+)-2,3-dihydro-5-[2-(dimethylamino)ethyl]-2-(4-fluorophenyl)-3-(2-thenoyloxy)-1,5-benzothiazepine-4(5H)-one Cis-(+)-2,3-dihydro-2-(4-methoxyphenyl)-3-nicotinoyloxy-5-[2-(dipropylamino)ethyl]-1,5-benzothiazepine-4(5H)-one Cis-(+)-2,3-dihydro-5-[2-(dimethylamino)ethyl]-2-(4-methoxyphenyl)-3-(4-methylbenzoyloxy)-1,5-benzothiazepine-4(5H)-one Cis-(+)-2,3-dihydro-5-[2-(diethylamino)ethyl]-2-(4-isopropoxyphenyl)-3-nicotinoyloxy-1,5-benzothiazepine-4(5H)-one Cis-(+)-2,3-dihydro-2-(4-chlorophenyl)-5-[2-(dimethylamino)ethyl]-3-(3,4,5-trimethoxybenzoyl]-1,5-benzothiazepine-4(5H)-one Cis-(+)-2,3-dihydro-2-(4-chlorophenyl)-3-(2,4-dichlorobenzoyloxy)-5-[2-(dimethylamino)ethyl]-1,5-benzothiazepine-4(5H)-one Cis-(+)-2,3-dihydro-5-[2-(dimethylamino)ethyl]-2-(4-methoxyphenyl)-3-(2-quinolylcarbonyloxy)-1,5-benzothiazepine-4(5H)-one Cis-(+)-2,3-dihydro-5-[2-(dimethylamino)ethyl]-2-(4-methoxyphenyl)-3-(2-piperidinylcarbonyloxy)-1,5-benzothiazepine-4(5H)-one Cis-(+)-2,3-dihydro-5-[2-dimethylaminoethyl]-2-(4-isopropoxyphenyl)-3-nicotinoyloxy-1,5-benzothiazepine-4(5H)-one

EXAMPLE 6

A sugar-coated tablet was prepared with
Compound of Example 1: 60 mg,
Sodium carboxymethylcellulose: 5 mg,
Magnesium stearate: 5 mg,
Gelatin: 5 mg,
Saccharose: 10 mg.
gum arabic, lactose, talc, titanium dioxide, aluminium lac according to conventional procedures.

EXAMPLE 7

A capsule was prepared with
Compound of Example 1: 80 mg,
Talc: 10 mg,
Lactose: 10 mg,
Sodium carboxymethylcellulose: 10 mg,
Starch q.s. to: 150 mg.

EXAMPLE 8

A tablet was prepared with
Compound of Example 1: 60 mg,
Levilite: 15 mg,
Starch: 15 mg,
Magnesium stearate: 8 mg,
Lactose: 15 mg,
Polyethyleneglycol: 6 mg.

We claim:

1. A 1,5-benzothiazepine compound of formula

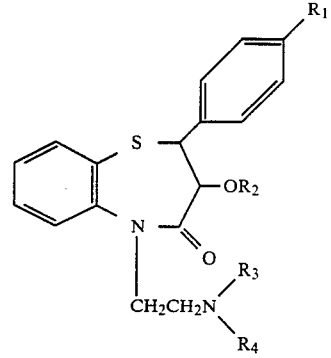

wherein:
$R_1$ is $(C_{1-4})$alkoxy;
$R_2$ is $R_5$—CO in which $R_5$ is pyrrolyl, furanyl, thienyl, pyridyl, quinolyl, pyrrolidinyl or piperidinyl;
$R_3$ and $R_4$ independently are $(C_{1-4})$alkyl and salts thereof with a pharmaceutically acceptable acid.

2. A compound as defined in claim 1, wherein $R_1$ is $(C_{1-4})$alkoxy, $R_2$ is the radical

in which $R_5$ is 3-pyridyl, $R_3$ and $R_4$ independently represent $(C_{1-4})$alkyl and salts therewith of pharmaceutically acceptable acids.

3. A compound as defined in claim 1, wherein $R_1$ represents $(C_{1-4})$alkoxy or a halogen atom, $R_2$ is benzoyl substituted with 1 to 3 $(C_{1-4})$alkoxy groups or halogen atoms, $R_3$ and $R_4$ independently represent $(C_{1-4})$alkyl, and salts therewith of pharmaceutically acceptable acids.

4. A compound as defined in claim 1, wherein $R_1$ represents $(C_{1-4})$alkoxy, $R_2$ stands for phenylcarbamoyl or phenylcarbamoyl substituted by 1 to 3 $(C_{1-4})$alkoxy groups or halogen atoms, $R_3$ and $R_4$ independently represent $(C_{1-4})$alkyl, and salts therewith of pharmaceutically acceptable acids.

5. A compound as defined in claim 1, which is 2,3-dihydro-5-[2-(dimethylamino)ethyl]-2-(4-methoxyphenyl)-3-nicotinoyloxy-1,5-benzothiazepine-4(5H)-one, and salts therewith of pharmaceutically acceptable acids.

6. A compound as defined in claim 1 which is cis-(+)-2,3-dihydro-5-[2-dimethylamino)ethyl]-2-(4-methoxyphenyl)-3-nicotinoyloxy-1,5-benzothiazepine-4(5H)-one, and salts therewith of pharmaceutically acceptable acids.

7. A pharmaceutical composition useful in the treatment of coronary diseases which contains about 50 to about 150 mg of an active ingredient which is a 1,5-benzothiazepine of formula

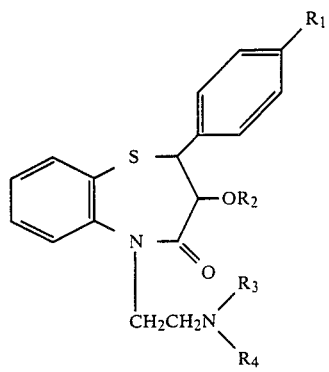 I wherein:
$R_1$ is $(C_{1-4})$alkoxy;
$R_2$ is

in which $R_5$ is pyrrolyl, furanyl, thienyl, pyridyl, quinolyl, pyrrolidinyl or piperidinyl;
$R_3$ and $R_4$ independently are $(C_{1-4})$alkyl and salts thereof with a pharmaceutically acceptable acid, in admixture with at least one solid or liquid carrier.

8. A pharmaceutical composition as defined in claim 7, wherein, in the active ingredient of formula I, $R_1$ is $(C_{1-4})$alkoxy, $R_2$ is the radical

in which $R_5$ is 3-pyridyl, $R_3$ and $R_4$ independently represent $(C_{1-4})$alkyl, and salts therewith of pharmaceutically acceptable acids.

9. A pharmaceutical composition as defined in claim 7, in which the active ingredient is 2,3-dihydro-5-[2-(dimethylamino)ethyl]-2-(4-methoxyphenyl)-3-nicotinoyloxy-1,5-benzothiazepine-4(5H)-one, and salts therewith of pharmaceutically acceptable acids.

10. A pharmaceutical composition as defined in claim 7 wherein the active ingredient is cis-(+)-2,3-dihydro-5-[2-(dimethylamino)ethyl]-3-nocotinoyloxy-1,5-benzothiazepine-4(5H)-one, and salts therewith of pharmaceutically acceptable acids.

11. A method for treating cardiovascular diseases due to coronary insufficiency, which comprises administering to warm-blooded animals suffering from said diseases an effective coronarodilating amount, varying from about 2 to about 5 mg/kg, of a 1,5-benzothiazepine of formula

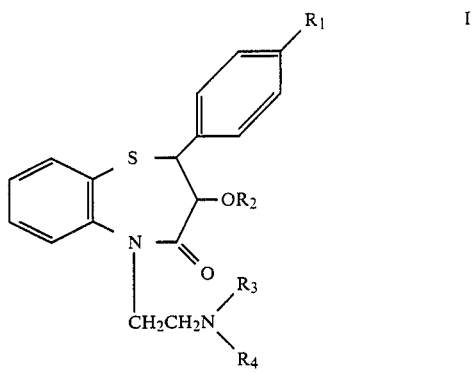 I or a salt therewith of pharmaceutically acceptable acids, wherein $R_1, R_2, R_3$ and $R_4$ are as defined in claim 1.

12. A method for treating cardiovascular diseases as defined in claim 11 wherein, in the 1,5-benzothiazepine of formula I, $R_1$ is $(C_{1-4})$alkoxy, $R_2$ is the group

in which $R_5$ represents pyrrolyl, furanyl, thienyl, quinolyl, pyrrolidinyl or piperidinyl, $R_3$ and $R_4$ independently represent $(C_{1-4})$alkyl, and salts therewith of pharmaceutically acceptable acids.

13. A method for treating cardiovascular diseases as defined in claim 12 wherein, in the 1,5-benzothiazepine of formula I, $R_1$ is $(C_{1-4})$alkoxy, $R_2$ is the radical

in which $R_5$ is 3-pyridyl, $R_3$ and $R_4$ independently represent $(C_{1-4})$alkyl, and salts therewith of pharmaceutically acceptable acids.

14. A method for treating cardiovascular diseases as defined in claim 12 wherein the administered compound is 2,3-dihydro-5-[2-(dimethylamino)ethyl)]-2-(4-methoxyphenyl)-3-nicotinoyloxy-1,5-benzothiazepine-4(5H)-one, and salts therewith of pharmaceutically acceptable acids.

15. A method for treating cardiovascular diseases as defined in claim 12 wherein the administered compound is cis-(+)-2,3-dihydro-5-[2-(dimethylamino)ethyl]-2-(4-methoxyphenyl)-3-nicotinoyloxy-1,5-benzothiazepine-4(5H)-one, and salts therewith of pharmaceutically acceptable acids.

* * * * *

UNITED STATES PATENT AND TRADEMARK OFFICE
CERTIFICATE OF CORRECTION

PATENT NO. : 4,547,495
DATED : October 15, 1985
INVENTOR(S) : Stefano Maiorana, Diego G. Brocchetti, Giuseppe Piacenza and Amedea Manfredi It is certified that error appears in the above-identified patent and that said Letters Patent are hereby corrected as shown below:

Title page, Item [75] should read as follows:

-- Inventors:  Stefano Maiorana, Milan;
Diego G. Brocchetti, Brescia;
Giuseppe Piacenza, Turin;
Amedea Manfredi, Milan; all of Italy. --.

Signed and Sealed this

Eighteenth Day of March 1986

[SEAL]

Attest:

DONALD J. QUIGG

Attesting Officer

Commissioner of Patents and Trademarks